United States Patent
Taniguchi et al.

(10) Patent No.: US 11,435,423 B2
(45) Date of Patent: Sep. 6, 2022

(54) IMAGE PROCESSING APPARATUS, MAGNETIC RESONANCE IMAGING APPARATUS INCLUDING THE SAME, AND MAGNETIC RESONANCE IMAGING SYSTEM

(71) Applicant: Hitachi, Ltd., Tokyo (JP)

(72) Inventors: Yo Taniguchi, Tokyo (JP); Yuki Kanazawa, Tokushima (JP); Masaharu Ono, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 330 days.

(21) Appl. No.: 16/675,482

(22) Filed: Nov. 6, 2019

(65) Prior Publication Data

US 2020/0142017 A1 May 7, 2020

(30) Foreign Application Priority Data

Nov. 6, 2018 (JP) .............................. JP2018-208813

(51) Int. Cl.
*G01R 33/56* (2006.01)
*G06T 7/00* (2017.01)
(Continued)

(52) U.S. Cl.
CPC .......... *G01R 33/5608* (2013.01); *A61B 5/055* (2013.01); *G01R 33/5602* (2013.01);
(Continued)

(58) Field of Classification Search
CPC ............ G01R 33/5608; G01R 33/5602; G01R 33/50; A61B 5/055; A61B 5/4041;
(Continued)

(56) References Cited

U.S. PATENT DOCUMENTS 9,993,156 B2 * 6/2018 Warntjes ................ A61B 5/055
2017/0345149 A1 * 11/2017 Warntjes ............ G01R 33/4828
2019/0219653 A1 * 7/2019 Shiodera .............. G01R 33/443

FOREIGN PATENT DOCUMENTS

JP 2011-024926 A 2/2011
JP 2013-539706 A 10/2013
(Continued)

OTHER PUBLICATIONS

Marco Ganzetti et al., Whole brain myelin mapping using T1- and T2-weighten MR imaging data, Methods Article, vol. 8, Article 671, pp. 1-14, Sep. 2, 2014.
(Continued)

*Primary Examiner* — Susan S Lee
(74) *Attorney, Agent, or Firm* — Mattingly & Malur, PC

(57) ABSTRACT

A myelin image is generated with a stable contrast regardless of an imaging condition with an MRI apparatus that measures an echo signal generated from a subject by applying a high-frequency magnetic field and a gradient magnetic field to the subject placed in a static magnetic field according to a predetermined imaging sequence. A reconstructed image is obtained from the echo signal. A distribution of a quantitative value of the subject is estimated using a plurality of the reconstructed images, each of which is obtained by a plurality of types of imaging having different imaging conditions of the imaging sequence, and a signal function defining a relationship between the quantitative value of the subject and a signal value of the reconstructed image. An image generation unit generates an arbitrary image from the distribution of the quantitative value.

6 Claims, 8 Drawing Sheets

(51) Int. Cl.
  *A61B 5/055* (2006.01)
  *G06T 11/00* (2006.01)
(52) U.S. Cl.
  CPC .......... *G06T 7/0012* (2013.01); *G06T 11/006*
    (2013.01); *G06T 2207/10016* (2013.01); *G06T*
      *2207/10088* (2013.01); *G06T 2207/30016*
        (2013.01)
(58) Field of Classification Search
  CPC ............ A61B 2576/026; G06T 7/0012; G06T
        11/006; G06T 2207/10016; G06T
      2207/10088; G06T 2207/30016; G06T
        7/0016; G06T 2200/04; G06T
          2207/10092
  See application file for complete search history.

(56) References Cited

FOREIGN PATENT DOCUMENTS

JP      2018-78959 A      5/2018
JP      2019122623 A   *  7/2019   ........... G01R 33/443

OTHER PUBLICATIONS

Japanese Office Action received in corresponding Japanese Application No. 2018-208813 dated May 17, 2022.

* cited by examiner

FIG. 5

| P | FA (DEGREE) | θ (DEGREE) | TR (second) |
|---|---|---|---|
| 1 | 10 | 8 | 0.03 |
| 2 | 40 | 2 | 0.01 |
| 3 | 40 | 2 | 0.04 |
| 4 | 40 | 5 | 0.01 |
| 5 | 40 | 7 | 0.01 |
| 6 | 40 | 22 | 0.03 |

T1

T2

R1 x R2

T1W / T2W

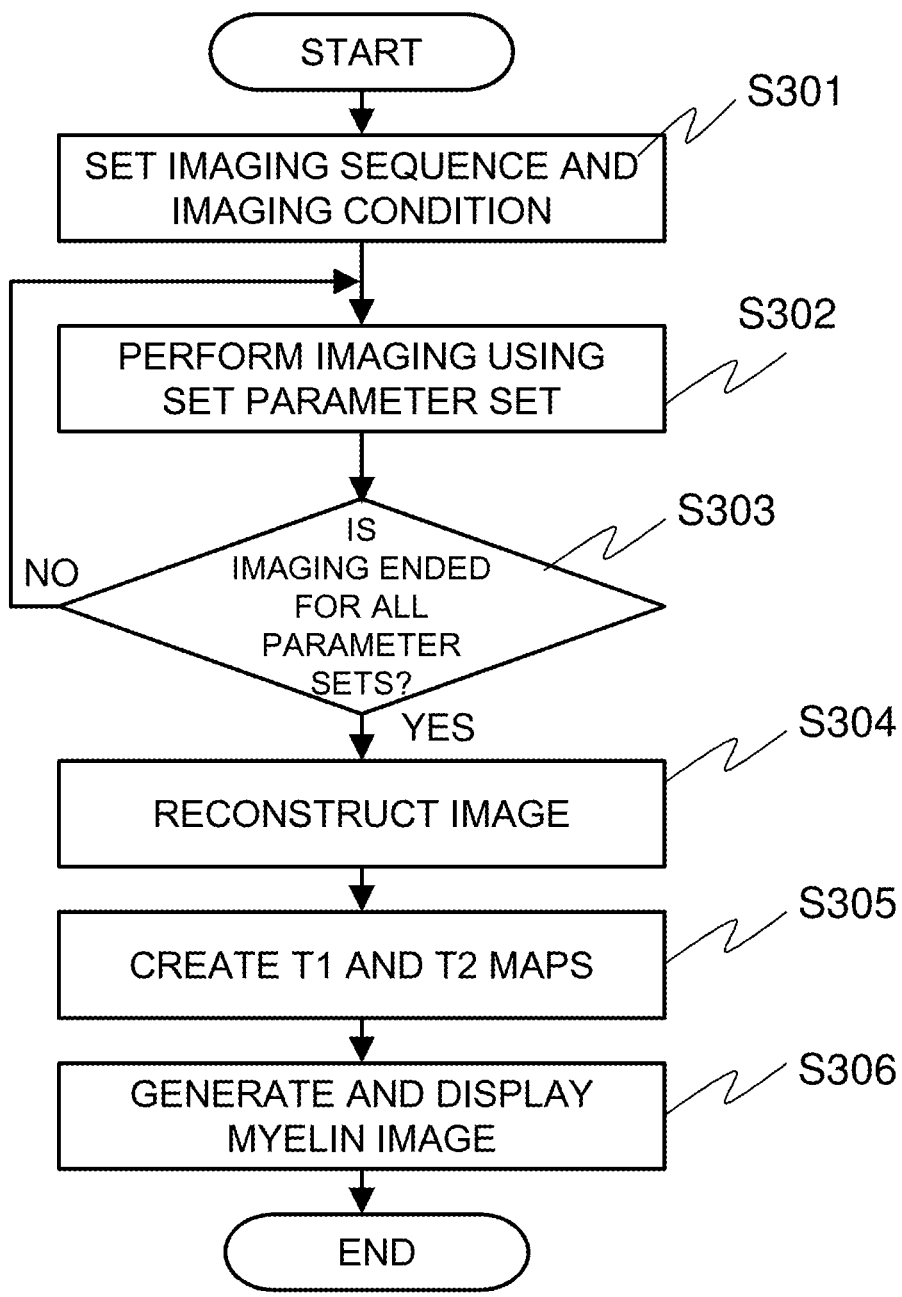

IMAGE PROCESSING APPARATUS, MAGNETIC RESONANCE IMAGING APPARATUS INCLUDING THE SAME, AND MAGNETIC RESONANCE IMAGING SYSTEM

INCORPORATION BY REFERENCE

The present application claims priority from Japanese patent application JP-2018-208813 filed on Nov. 6, 2018, the content of which is hereby incorporated by reference into this application.

BACKGROUND OF THE INVENTION

Field of the Invention

The present invention relates to a magnetic resonance imaging apparatus, an image processing apparatus, and a magnetic resonance imaging system, and more particularly relates to a magnetic resonance imaging apparatus, an image processing apparatus, and a magnetic resonance imaging system for generating a myelin image by calculation.

Description of the Related Art

A magnetic resonance imaging (MRI) apparatus is a medical diagnostic imaging apparatus that obtains an image of a subject by causing nuclear magnetic resonance in a specific nucleus, typically a hydrogen nucleus, contained in a tissue of the subject, receiving a generated nuclear magnetic resonance signal (echo signal), and reconstructing an image from the received nuclear magnetic resonance signal.

An intensity of the nuclear magnetic resonance signal obtained by the MRI apparatus largely depends on the spin density of hydrogen nuclei in the tissue, and varies due to an apparatus condition, an imaging condition such as a pulse sequence or an imaging parameter used for imaging, and a factor on the subject side such as a tissue characteristic of the subject.

The apparatus condition corresponds to a magnetic field intensity, a reception sensitivity distribution, etc., which are collectively referred to as apparatus parameters. In addition, examples of the imaging parameter include a repetition time, a set intensity of a high-frequency magnetic field, a phase of the high-frequency magnetic field, etc. Examples of the factor on the subject side include a longitudinal relaxation time, a transverse relaxation time, a resonance frequency, a diffusion coefficient, an irradiation intensity distribution of a high-frequency magnetic field, etc. These factors, in addition to the spin density, are inclusively called as a subject parameter.

There is a method of obtaining a value of a specific parameter among a plurality of parameters that determines the intensity of the nuclear magnetic resonance signal by computation between images using a signal function indicating a relationship between the parameter value and the signal intensity and setting the parameter value as a pixel value (JP-A-2011-024926). An image obtained by this method is referred to as a computation image, a quantitative value image, etc.

Incidentally, in recent years, a method for acquiring a myelin image having a contrast corresponding to the amount of myelin by MRI has attracted attention. Myelin is a phospholipid layer that exists around a nerve cell axon, and the presence of myelin is considered to increase a speed of a signal flowing through the axon by double digits. In addition, it is known that myelin increases with brain development. A disease in which myelin is destroyed is referred to as a demyelinating disease, and a representative thereof is multiple sclerosis. A myelin image is useful for diagnosing the disease and evaluating a therapeutic agent that regenerates myelin.

There is a known method for generating a myelin image by computing a ratio of a T1-weighted image to a T2-weighted image. While this method has an advantage that a myelin image can be easily obtained, pixel values of the T1-weighted image and the T2-weighted image change variously depending on the imaging conditions, so that there is a problem that the contrast of the myelin image is not constant. Therefore, "Ganzetti M, Wenderoth N, Mantini D, Whole brain myelin mapping using T1- and T2-weighted MR imaging data, Frontiers in Human Neuroscience, 2014, 671." (referred as a non-patent document 1 hereinafter) proposes a method of adjusting the contrast between the T1-weighted image and the T2-weighted image to be constant using a histogram.

However, as described above, the pixel value of each pixel of the T1-weighted image or the T2-weighted image varies depending on the imaging conditions such as TE and TR even when an imaging sequence is the same. That is, each pixel value of the T1-weighted image and the T2-weighted image is determined by the parameters. For this reason, when the contrast is simply adjusted as in the method described in the non-patent document 1, the myelin images generated from the T1-weighted image and the T2-weighted image taken under different imaging conditions may not be the same.

SUMMARY OF THE INVENTION

The invention has been made in view of the above circumstances, and an object thereof is to generate a myelin image with stable contrast regardless of an imaging condition.

To solve the above problem, the invention provides the following means.

An aspect of the invention provides an MRI apparatus including a measurement unit that measures an echo signal generated from a subject by applying a high-frequency magnetic field and a gradient magnetic field to the subject placed in a static magnetic field according to a predetermined imaging sequence, an image reconstruction unit that obtains a reconstructed image from the echo signal, a parameter estimation unit that estimates a distribution of a quantitative value of the subject using a plurality of reconstructed images, each of which is obtained by a plurality of types of imaging having different imaging conditions of the imaging sequence, and a signal function defining a relationship between the quantitative value of the subject and a signal value of the reconstructed image, and an image generation unit that generates an arbitrary image from the distribution of the quantitative value, in which the parameter estimation unit estimates a longitudinal relaxation speed or a longitudinal relaxation time and a transverse relaxation speed or a transverse relaxation time as the quantitative value, and the image generation unit generates a myelin image according to a function having a longitudinal relaxation speed or a longitudinal relaxation time and a transverse relaxation speed or a transverse relaxation time obtained as variables.

Another aspect of the invention provides an image processing apparatus including a quantitative value distribution acquisition unit that acquires a distribution of a quantitative value of a subject, and an image generation unit that obtains a myelin image according to a function having a longitudinal relaxation speed or a longitudinal relaxation time and a transverse relaxation speed or a transverse relaxation time obtained from the distribution of the quantitative value as variables.

Still another aspect of the invention provides an MRI system including an MRI apparatus including a measurement unit that measures an echo signal generated from a subject by applying a high-frequency magnetic field and a gradient magnetic field to the subject placed in a static magnetic field according to a predetermined imaging sequence, and an image reconstruction unit that obtains a reconstructed image from the echo signal, and the image processing apparatus.

According to the invention, it is possible to generate a myelin image with a stable contrast regardless of an imaging condition.

BRIEF DESCRIPTION OF THE DRAWINGS

FIG. 5 is an example of a parameter set used for estimation of a parameter value;

FIG. 6A is a T1 map, FIG. 6B is a T2 map, FIG. 6C is a myelin image (R1×R2) generated by the MRI apparatus of the present embodiment, and FIG. 6D is a reference diagram illustrating an example of a conventional myelin image (T1 W/T2 W);

FIG. 7 is a flowchart illustrating a flow of a process of generating a myelin image in the MRI apparatus according to the embodiment of the invention.

DETAILED DESCRIPTION OF THE INVENTION

First Embodiment

Hereinafter, a magnetic resonance imaging apparatus (hereinafter, simply referred to as "MRI apparatus") according to an embodiment of the invention will be described with reference to drawings.

Figure 1:
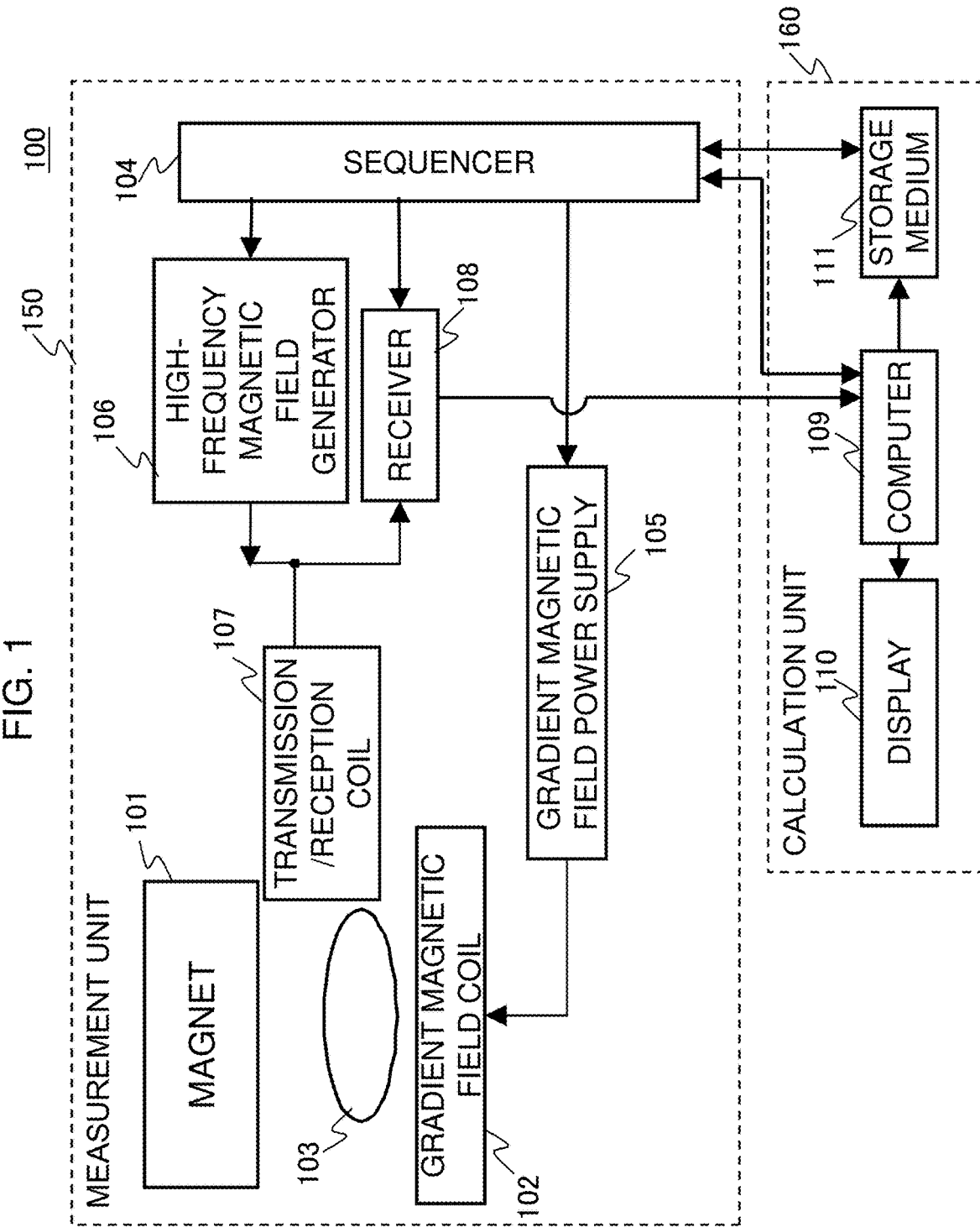
FIG. 1 is a block diagram illustrating a schematic configuration of an MRI apparatus according to an embodiment of the invention.

FIG. 1 illustrates a schematic configuration of the MRI apparatus according to the present embodiment. The MRI apparatus 100 includes a measurement unit 150 that applies a high-frequency magnetic field and a gradient magnetic field to a subject placed in a static magnetic field according to a predetermined imaging sequence and measures an echo signal generated from the subject, and a calculation unit 160 that performs various calculation processes on the echo signal measured by the measurement unit 150.

The measurement unit 150 includes a magnet 101 that generates a static magnetic field, a gradient magnetic field coil 102 that generates a gradient magnetic field, a sequencer 104, a gradient magnetic field power supply 105, a high-frequency magnetic field generator 106, a transmission/reception coil 107 that irradiates a high-frequency magnetic field and detects a nuclear magnetic resonance signal, and a receiver 108. In an example illustrated in FIG. 1, the transmission/reception coil 107 is a single one. However, a transmission coil and a reception coil may be separately provided.

The calculation unit 160 includes a computer 109, a display 110, and a storage medium 111.

The subject 103 is placed on a bed (table) in a static magnetic field space generated by the magnet 101. In addition, the sequencer 104 sends commands to the gradient magnetic field power supply 105 and the high-frequency magnetic field generator 106 to generate a gradient magnetic field and a high-frequency magnetic field, respectively. The high-frequency magnetic field is applied to the subject 103 through the transmission/reception coil 107.

A nuclear magnetic resonance signal (echo signal) generated from the subject 103 is received by the transmission/reception coil 107 and detected by the receiver 108. The sequencer 104 sets a nuclear magnetic resonance frequency (detection reference frequency f0) as a reference for detection. The detected signal is sent to the computer 109 to perform signal processing such as image reconstruction. A result thereof is displayed on the display 110. The detected signal and a measurement condition can be stored in the storage medium 111 as necessary.

The sequencer 104 normally performs control so that each device operates at a timing and intensity programmed in advance. Among programs, particularly, a program that describes the high-frequency magnetic field, gradient magnetic field, signal reception timing and intensity is referred to as a pulse sequence (imaging sequence). The imaging sequence will be described later.

The computer 109 includes a central processing unit 119 and a memory 120, and controls the entire MRI apparatus 100. That is, the computer 109 functions as a calculation device that operates each unit of the measurement unit 150 according to the pulse sequence and performs various signal processing on the echo signal obtained by imaging to obtain a desired image. In the present embodiment, the computer 109 estimates a distribution of quantitative values of the subject based on a plurality of reconstructed images obtained by a plurality of types of imaging with different imaging conditions of the imaging sequence, and generates a myelin image from the distribution of quantitative values.

Figure 2:
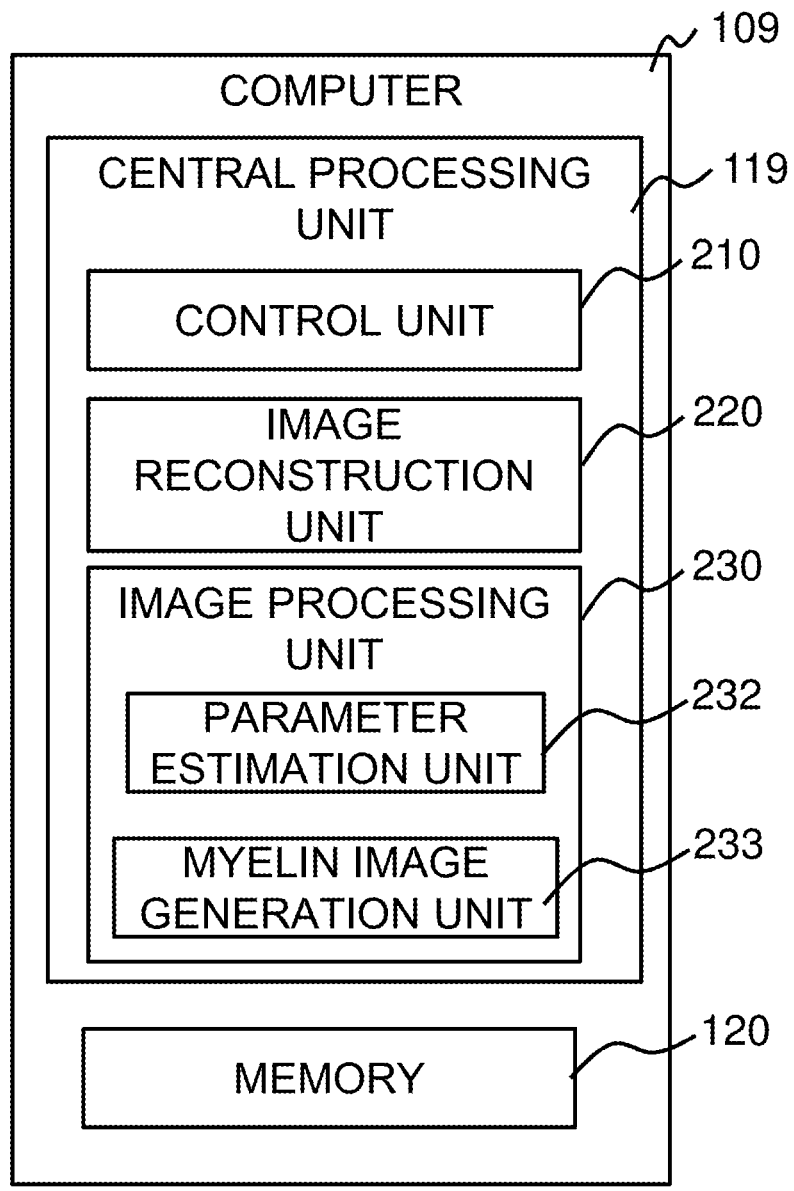
FIG. 2 is an explanatory diagram illustrating a schematic configuration of a computer in the MRI apparatus of FIG. 1.

For realizing these functions, as illustrated in FIG. 2, the central processing unit 119 of the computer 109 functions as an image reconstruction unit 220 that obtains a reconstructed image from the echo signal measured by the measurement unit 150, an image processing unit 230 that generates a desired image using the reconstructed image created by the image reconstruction unit 220, and a control unit 210 that controls the entire MRI apparatus 100 including the image reconstruction unit 220, the image processing unit 230, and the measurement unit 150. In addition, the image processing unit 230 functions as a parameter estimation unit 232 that estimates the quantitative value distribution of the subject and a myelin image generation unit 233 that generates a myelin image from the quantitative value distribution.

Respective functions of the control unit 210, the image reconstruction unit 220, and the image processing unit 230 realized by these central processing unit 119 can be realized as software by the central processing unit 119 reading a program stored in a memory such as the storage medium 111 into the memory 120 and executing the program.

In addition, some or all of operations performed by each unit included in the central processing unit 119 can be implemented by hardware such as a programmable logic device (PLC), an application specific integrated circuit (ASIC), or a field-programmable gate array (FPGA).

The parameter estimation unit 232 and the myelin image generation unit 233 can be realized by a computer provided independently of the MRI apparatus 100, such as an image processing apparatus capable of transmitting and receiving data to and from the computer 109 of the MRI apparatus 100. Further, the computer 109 can include an input device such as a mouse and a track pad for accepting setting of an imaging condition by a user, etc. (not illustrated).

Hereinafter, a detailed description will be given of the parameter estimation unit 232 that estimates the quantitative value distribution of the subject and the myelin image generation unit 233 that generates the myelin image from the quantitative value distribution, which are included in the image processing unit 230.

The parameter estimation unit 232 acquires, for example, a T1 map or an R1 map, and a T2 map or an R2 map as the quantitative value distribution. Specifically, for example, the parameter estimation unit 232 estimates a longitudinal relaxation time T1 or a longitudinal relaxation speed R1=1/T1 and a transverse relaxation time T2 or a transverse relaxation speed R2=1/T2 as quantitative values using the reconstructed image obtained by the image reconstruction unit 220 and the signal function determined by the imaging sequence used when acquiring the reconstructed image, and estimates the T1 map or the R1 map, and the T2 map or the R2 map as the quantitative value distribution.

Here, the quantitative value is at least one of a parameter depending on the subject (subject parameter) and an apparatus-specific parameter (apparatus parameter) among parameters that determine a signal value, and T1 and T2 are subject parameters.

In addition to T1 and T2, examples of the subject parameter include a spin density ($\rho$), a resonance frequency difference ($\Delta f0$), a diffusion coefficient (D), etc. The resonance frequency difference $\Delta f0$ is a difference between a resonance frequency and a reference frequency f0 of each pixel. Examples of the apparatus parameter include a static magnetic field intensity (B0), a irradiation intensity distribution (B1) of a high-frequency magnetic field, a sensitivity distribution (Sc) of a reception coil, etc. The irradiation intensity distribution B1 and the sensitivity distribution Sc are parameters that depend not only on the apparatus but also on the subject.

Besides the subject parameter and the apparatus parameter described above, the parameter that determines each signal value (pixel value) of the reconstructed image include imaging parameter (s) that can be arbitrarily set by the user. Examples of the imaging parameters include a repetition time (TR), an echo time (TE), a setting intensity (flip angle (FA)) of the high-frequency magnetic field, a phase ($\theta$) of the high-frequency magnetic field, etc.

The signal function is a function that represents a relationship between these parameters and the signal value, and can be analytically obtained when the imaging sequence is determined. Further, a sequence that may not be analytically obtained can be obtained by numerical simulation as disclosed in JP-A-2011-024926. In the present embodiment, the parameter estimation unit 232 estimates T1 and T2 as quantitative values using a signal function obtained by numerical simulation.

That is, the parameter estimation unit 232 estimates T1 and T2 corresponding to subject parameter values as quantitative values of each pixel using a signal function generated in advance for each imaging sequence by numerical simulation and stored in the memory 120 or another storage device, and estimates a T1 map and a T2 map as distributions of quantitative values.

(Generation of Signal Function)

Here, the signal function used by the parameter estimation unit 232 will be described.

As described above, the signal function used by the parameter estimation unit 232 when estimating the parameter value can be generated in advance by numerical simulation and stored in the storage medium 111 or the memory 120. The signal function may be generated by the computer 109 or may be generated by another calculation device, etc. The signal function can be generated, for example, by a technology disclosed in JP-A-2011-024926.

Specifically, first, a signal function shown in the following Equation (1) is created by numerical simulation. When it is presumed that FA (flip angle), TR (repetition time), TE (echo time), and $\theta$ (RF phase increment value) are given as imaging parameters, a signal function fs representing the signal intensity of each pixel is expressed as follows.

[Equation 1]

$$I = fs(\rho, T1, T2, B1, FA, TR, TE, \theta, Sc) \\ = \rho Sc\exp(-TE/T2)f(T1, T2, B1 \times FA, \theta, TR) \quad (1)$$

In Equation (1), T1 is a longitudinal relaxation time, T2 is a transverse relaxation time, $\rho$ is a spin density, B1 is an RF irradiation intensity, and Sc is a sensitivity of the reception coil.

When the echo signal obtained by imaging is a gradient echo illustrated in FIG. 3 (details will be described later), the transverse relaxation time T2 becomes an apparent transverse relaxation time T2*. Which of T2 and T2* is obtained depends on the imaging sequence and is not affected by a parameter estimation method. Therefore, the transverse relaxation time and the apparent transverse relaxation time are not distinguished from each other and are expressed as T2 hereinafter.

Here, in the signal function fs, B1 is a coefficient of FA at the time of image capturing, and thus is converted into a form of product with FA. In addition, $\rho$ and Sc act on the signal intensity as proportional coefficients, and thus are put out of the function, and TE also affects the signal intensity in the form of an exponential function, and thus is similarly put out of the function.

The imaging parameters FA, TR, and $\theta$ are comprehensively changed with respect to arbitrary values of the subject parameters T1 and T2 to create a signal by numerical simulation, and a signal function is created by interpolation. The spin density $\rho$, B1, and Sc to be imaged are presumed to be constant (for example, set to 1).

Ranges in which the imaging parameter and the subject parameter are comprehensively changed is set to include a range of the imaging parameter used for actual imaging and a range of T1 and T2 of the subject, respectively. Examples of parameter ranges and values to be changed are shown below.

Four TRs [ms]: 10, 20, 30, and 40
Ten FAs [degree]: 5, 10, 15, 20, 25, 30, 35, 40, 50, and 60
Seventeen θs [degree]: 0, 1, 2, 3, 4, 5, 6, 7, 8, 9, 10, 12, 14, 16, 18, 20, and 22
Seventeen T2s [s]: 0.01, 0.02, 0.03, 0.04, 0.05, 0.07, 0.1, 0.14, 0.19, 0.27, 0.38, 0.53, 0.74, 1.0, 1.4, 2.0, and 2.8
Fifteen T1s [s]: 0.05, 0.07, 0.1, 0.14, 0.19, 0.27, 0.38, 0.53, 0.74, 1.0, 1.5, 2.0, 2.8, 4.0, and 5.6

In the above example, 173,400 imaging parameter sets are configured from all combinations of imaging parameters and subject parameters. For these imaging parameter sets, each signal value is calculated by computer simulation.

In numerical simulation, a subject model in which spins are arranged on lattice points, an imaging sequence, an imaging parameter, and an apparatus parameter are input, and a Bloch equation, which is a basic equation of a magnetic resonance phenomenon, is solved to output a magnetic resonance signal. The subject model is given as a spatial distribution of spins (γ, M0, T1, T2). Here, γ is a gyromagnetic ratio, and M0 is thermal equilibrium magnetization (spin density). An image under a given condition can be obtained by reconstructing an image of the magnetic resonance signal.

The Bloch equation is a first-order linear ordinary differential equation and is expressed by the following Equation (2).

[Equation 2]

$$\frac{d}{dt}\begin{pmatrix} M_x \\ M_y \\ M_z \end{pmatrix} = \begin{pmatrix} -1/T2 & \gamma H & \\ -\gamma H & -1/T2 & \gamma H1 \\ & -\gamma H1 & -1/T1 \end{pmatrix}\begin{pmatrix} M_x \\ M_y \\ M_z \end{pmatrix} + \begin{pmatrix} 0 \\ 0 \\ M0/T1 \end{pmatrix} \quad (2)$$

$$H = B_0 + G_x x + G_y y + G_z z + 2\pi\Delta f_0/\gamma$$

Here, (x, y, z) represents a three-dimensional (3D) orthogonal coordinate system, and z is equal to a direction of a static magnetic field (intensity is B0). Further, (Mx, My, Mz) is spin, each of Gx, Gy, and Gz is a gradient magnetic field intensity in a subscript direction, H1 is high-frequency magnetic field intensity, and Δf0 is a frequency of a rotating coordinate system.

A signal function fs is constructed by interpolation from a signal value obtained by computer simulation. For the interpolation, it is possible to use linear interpolation of about first to third orders or spline interpolation.

Figure 4:
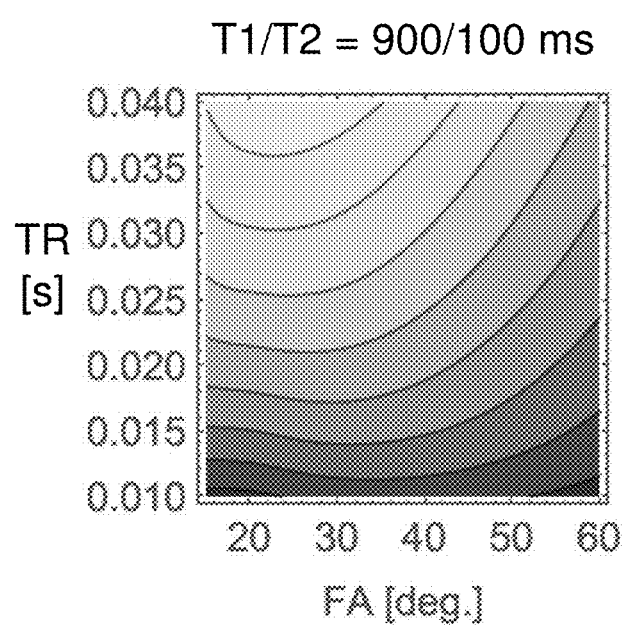
FIG. 4 is a graph showing a part of an intensity of a signal function.

A part of the intensity of the signal function created as described above is shown in FIG. 4. In FIG. 4, a horizontal axis and a vertical axis are displayed as FA and TR, respectively, for T1=900 ms, T2=100 ms, and θ=5 degrees.

(Estimation of Parameter Value)

Next, the parameter estimation unit 232 estimates at least one of the subject parameter and the apparatus parameter using the above-described signal function fs and a plurality of reconstructed images obtained by a plurality of types of imaging with different imaging conditions. That is, T1 and T2 are estimated using a reconstructed image captured with a plurality of parameter sets in which at least one of a plurality of imaging parameters is different and the signal function fs calculated by numerical simulation.

FIG. 5 illustrates an example of the parameter sets. The imaging parameter sets from P1 to P6 illustrated in FIG. 5 include combinations in each of which FA is 10 degrees or 40 degrees, the phase increment θ is 2, 5, 7, 8, or 22 degrees, and the repetition time TR is 10 ms, 30 ms, or 40 ms, respectively. In addition, in the imaging sequence, all TEs in the case of gradient echo are 2 ms. The imaging sequence is an RF-spoiled GE sequence illustrated in FIG. 3.

It is sufficient that the number of parameter sets is greater than the number of values of the subject parameters and the apparatus parameters to be estimated, which are unknown numbers, and is not limited to the above example. The estimation accuracy improves as the number of parameter sets (number of images) increases. However, the imaging time becomes longer accordingly.

Specifically, a signal value I for each pixel in the plurality of reconstructed images is fit to a function f expressed by the following Equation (3) obtained by modifying Equation (1), and the parameter value(s) is estimated.

[Equation 3]

$$I = a\,\exp(-TE/T2) f(T1, T2, \theta, B1 \times FA, TR)$$

$$a = \rho S_c \quad (3)$$

The function fitting can be performed by a least square method expressed by the following Equation (4).

[Equation 4]

$$\sum_{FA,\Delta\theta,TR}\{I(FA, \theta, TR, TE) - a\exp(-TE/T2)f(T1, T2, \theta, B1 \times FA, TR)\}^2 = \min \quad (4)$$

Here, I is a pixel value of an image in a predetermined parameter set (FA, θ, TR, TE). By performing the above estimation on the signal value (pixel value) for each pixel, a parameter map (parameter image) is obtained for each parameter. The myelin image is generated as a product of the inverse of the longitudinal relaxation time T1 and the inverse of the transverse relaxation time T2. Therefore, in the present embodiment, a T1 map and a T2 map are obtained.

The myelin image generation unit 233 acquires an image having a value corresponding to the amount of myelin as a pixel value based on the T1 map and the T2 map estimated by the parameter estimation unit 232.

Specifically, the myelin image generation unit 233 generates a myelin image by substituting each pixel value of the T1 map and the T2 map into the following Equation (5).

[Equation 5]

$$(\text{Myelin image}) = f_1(T_1, T_2) = 1/T_1 \times 1/T_2 \quad (5)$$

A reason why Expression (5) has an image contrast reflecting the amount of myelin is as follows.

In the non-patent document 1, a myelin image is obtained by division T1 W/T2 W of a T1-weighted image (T1 W) and a T2-weighted image (T2 W). A luminance value of T1 W is smaller as T1 is longer, and a luminance value of T2 W is larger as T2 is longer.

That is, the image contrast of T1 W is close to 1/T1, and T2 W is close to T2. From this fact, it has been found that Equation (5) holds from the following approximate Expression (6).

[Equation 6]

$$(\text{Myelin image}) = T_1 W/T_2 W \approx (1/T_1)/T_2 = 1/T_1 \times 1/T_2 \quad (6)$$

As described above, the myelin image can be generated by a function f1 (T1, T2) for obtaining the product of the reciprocals of T1 and T2.

Note that it is possible to obtain a myelin image with the same contrast using T2* which is an apparent transverse relaxation time instead of T2. Alternatively, a polynomial for obtaining T2 in advance from the proton density, T1, and T2* may be generated, and T2 may be synthesized using this polynomial.

The reciprocals of T1 and T2 are the longitudinal relaxation speed R1 and the transverse relaxation speed R2, respectively. Therefore, Equation 5 can be transformed into Equation 7.

[Equation 7]

$$(\text{Myelin image}) = f_2(R_1, R_2) = R_1 \times R_2 \quad (7)$$

That is, the myelin image can be generated by a function f2 (R1, R2) for obtaining the product of the longitudinal relaxation speed and the transverse relaxation speed. Note that it is possible to obtain a myelin image with the same contrast using R2*, which is an apparent transverse relaxation speed, instead of R2.

Figure 6A:
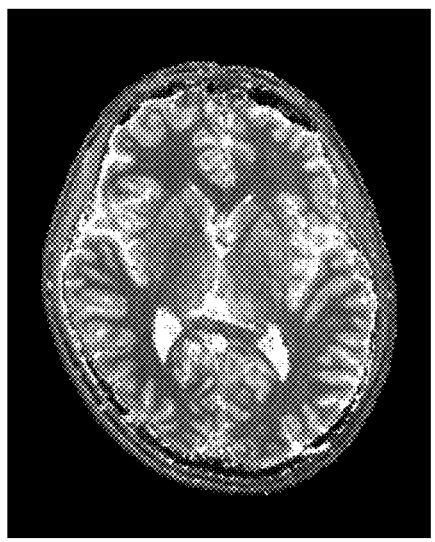
FIGS. 6A to 6D are reference diagrams illustrating an example of a quantitative value distribution and an image obtained from the quantitative value distribution, in which specifically.
Figure 6B:
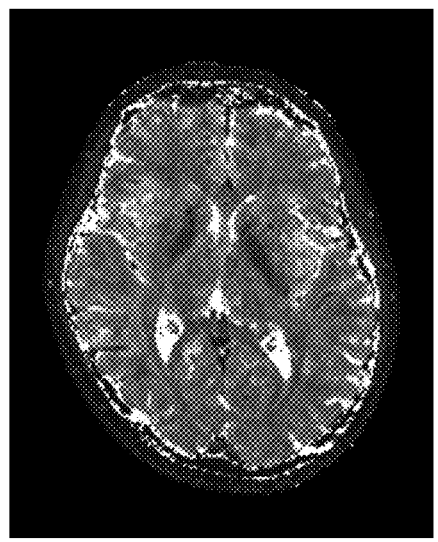
Figure 6C:
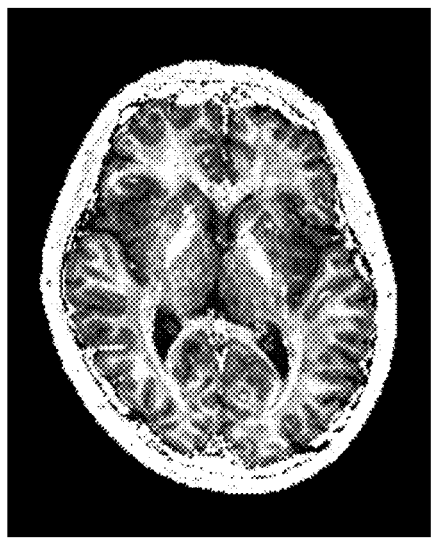
Figure 6D:
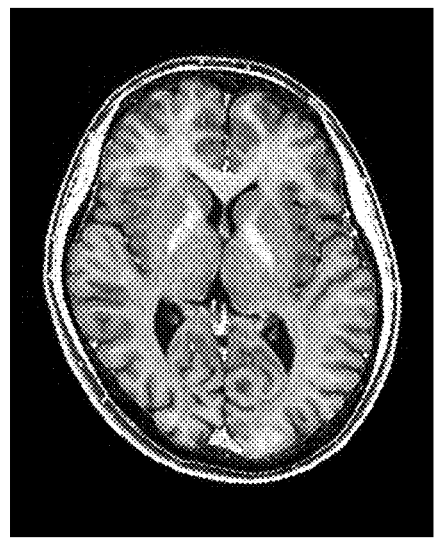

FIG. 6A illustrates a T1 map, FIG. 6B illustrates a T2 map, FIG. 6C illustrates a myelin image (R1×R2) generated by the MRI apparatus of the present embodiment, and FIG. 6D illustrates an example of a conventional myelin image (T1 W/T2 W). From the myelin image (R1×R2 image) of FIG. 6C, it can be seen that the brightness of the white matter is increased and an image contrast reflecting the amount of myelin is obtained as in the conventional case. In addition, since the contrast between white matter and gray matter is stronger than that of the conventional myelin image illustrated in FIG. 6D, it can be understood that the myelin image generated by the MRI apparatus according to the present embodiment is an image that greatly reflects the amount of myelin.

Hereinafter, a description will be given of a flow of imaging for obtaining a myelin image by estimating the T1 map and the T2 map in the MRI apparatus according to the present embodiment with reference to a flowchart of FIG. 7.

In step S301, when the control unit 210 receives selection of an imaging sequence or setting of an imaging condition by the user via an input device (not illustrated), etc., the control unit 210 sends a command according to the set imaging sequence and imaging condition to the sequencer 104.

In the present embodiment, to obtain a distribution of parameter values, for example, a plurality of parameter sets, in which at least one of a plurality of imaging parameters is made different, illustrated in FIG. 5 is set. The parameter sets may be preset with a plurality of combinations, or may be arbitrarily changed or selected by the user.

Subsequently, in step S302, the sequencer 104 controls each unit of the measurement unit 150 so that imaging is performed under the set imaging condition (parameter set), and the measurement unit 150 measures an echo signal according to the set imaging sequence and disposes the measured echo signal in a k-space.

Figure 3:
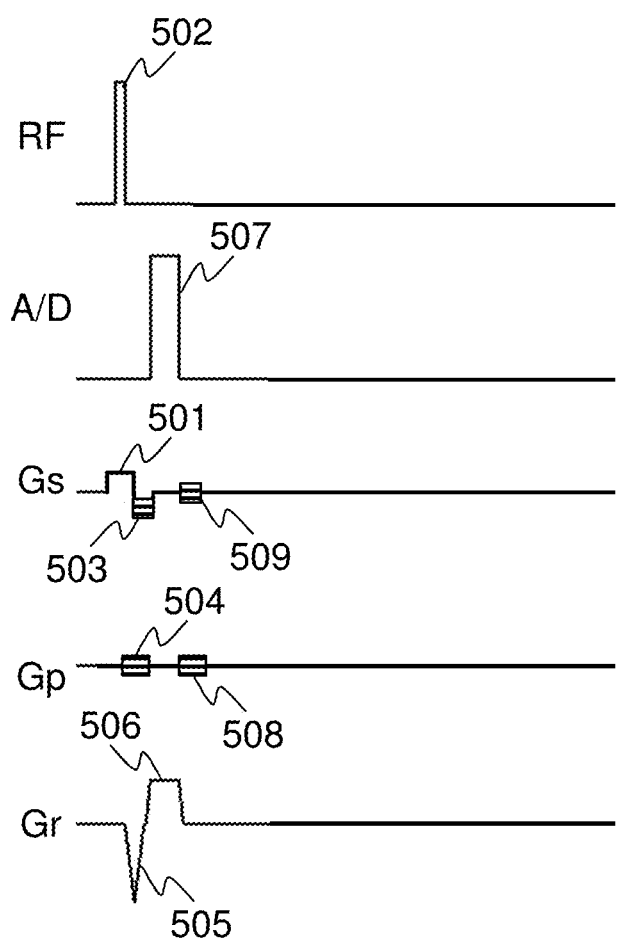
FIG. 3 is a timing chart illustrating an example of a gradient echo (imaging sequence)

Here, FIG. 3 illustrates an example of an imaging sequence used for acquiring a parameter value distribution. In FIG. 3, RF, A/D, Gs, Gp, and Gr represent a high-frequency magnetic field, signal reception, a slice gradient magnetic field, a phase encoding gradient magnetic field, and a readout gradient magnetic field, respectively. This imaging sequence is an RF-spoiled GE sequence, and a pixel value of an image obtained by this imaging sequence mainly depends on subject parameters T1 and T2* (apparent transverse relaxation time), ρ, and apparatus parameters B1 and Sc.

In this pulse sequence, first, a slice gradient magnetic field pulse 501 is applied and a high-frequency magnetic field (RF) pulse 502 is irradiated to excite magnetization of a certain slice in a target object. Subsequently, while applying a readout gradient magnetic field pulse 506 for providing position information in a readout direction after applying a slice encoding gradient magnetic field pulse 503 for giving position information in a slice direction and performing rephase, a phase encoding gradient magnetic field pulse 504 for giving position information in a phase encoding direction to a phase of magnetization, and a readout gradient magnetic field pulse 505 for dephasing, a magnetic resonance signal (gradient echo) is measured during a signal reception time 507. Then, finally, a phase encoding gradient magnetic field pulse 508 for dephasing and a slice gradient magnetic field pulse 509 for dephasing are applied.

The measurement unit 150 repeats the above procedure for a repetition time TR, and measures echoes a plurality of times. Intensities (phase encoding amount kp) of the phase encoding gradient magnetic field pulses (504, 508) and intensities (slice encoding amount ks) of the slice encoding gradient magnetic field pulses (503, 509) are changed for each repetition, and an increment value of a phase of an RF pulse is changed by $\theta_0$ (a phase of an nth RF pulse is $\theta(n)=(n-1)+\theta_0 \times n$). Each echo is disposed in a 3D k-space.

The measurement unit 150 repeats the measurement of the echo signal described above until measurement of the planned number of parameter sets is completed while changing the parameter set, and acquires pieces of k-space data, the number of which is the same as the number of parameter sets (step S303).

In step S304, the image reconstruction unit 220 reconstructs an image by performing 3D inverse Fourier transform on the collected k-space data. Here, the same number of reconstructed images as the number of parameter sets is obtained.

Subsequently, in step S305, the parameter estimation unit 232 estimates a subject parameter value using a signal function stored in advance and a plurality of images created by the image reconstruction unit 220. That is, the parameter estimation unit 232 calculates the values of the subject parameters T1 and T2 for each pixel, and generates T1 and T2 maps. In step S306, the myelin image generation unit 233 generates a myelin image from the T1 map and the T2 map, and displays the generated myelin image on the display 110.

As described above, according to the present embodiment, since the myelin image is synthesized using the quantitative values T1 and T2 or R1 and R2, a stable image contrast can be obtained regardless of the imaging condition. In the present embodiment, an example in which the parameter estimation unit 232 estimates a quantitative value to generate a quantitative value distribution has been described. However, a method of acquiring the quantitative value distribution is not limited thereto, and the quantitative value distribution may be acquired by receiving an input of a previously generated quantitative value distribution.

Second Embodiment

In the first embodiment described above, a method for obtaining quantitative values such as T1 and T2 using numerical simulation when the signal function may not be analytically obtained has been described. Here, an example of a more general case where the signal function is analytically obtained will be given.

It is known that a pixel value (transverse magnetization intensity Mxy) of FLASH, which is one of gradient echo system sequences, is expressed by the following Equation (8).

[Equation 8]

$$M_{1xy} = a_1 \frac{1 - \exp(-TR/T_1)}{1 - \cos FA \cdot \exp(-TR/T_1)} \sin FA \quad (8)$$

Here, TR and α are imaging parameters, which are a repetition time and a flip angle, respectively. T1 is the longitudinal relaxation time of the subject parameter.

In a spin echo (SE) method, when TR is sufficiently longer than T1, a pixel value is expressed by the following Equation (9).

[Equation 9]

$$M_{2xy} = a_2 \exp(-TE/T_2) \quad (9)$$

Here, TE is an echo time of an imaging parameter, and T2 is a longitudinal relaxation time of a subject parameter.

Using these equations, a1, a2, T1, and T2 can be estimated.

In the case of obtaining the subject parameter T1 using FLASH of Equation (8), the following is performed. Using FLASH, TR is set to 100 ms, and FA is set to 30° and 60°, and two images A and B are captured. For each pixel, a value of the image A and a value of the image B are fit to Equation (8) using the least square method, etc. to obtain a1 and T1.

In the case of obtaining the subject parameter T2 using an SE of Equation (9), the following is performed. Two images A and B are captured using an SE in which TR is sufficiently longer than T1 by setting TE to 20 ms and 40 ms. For each pixel, a value of the image A and a value of the image B are fit to Equation (9) using the least square method, etc. to obtain a2 and T2.

According to the non-patent document 1, the myelin image is T1 W/T2 W. T1 W and T2 W can be synthesized by appropriately substituting a, T1, and T2 calculated by the above-described method into Equation (10) or Equation (11). That is, the following Equations (10) and (11) are established.

[Equation 10]

$$T1W = a_{1\,or\,2} \frac{1 - \exp(-TR/T_1)}{1 - \cos FA \cdot \exp(-TR/T_1)} \sin FA \quad (10)$$

[Equation 11]

$$T2W = a_{1\,or\,2} \exp(-TE/T_2) \quad (11)$$

Here, TR, FA, and TE are constants, and may be set to, for example, 300 ms, 90 degrees, and 100 ms, respectively. Therefore, the myelin image can be obtained according to the following Equation (12).

[Equation 12]

$$(\text{Myelin image}) = T1W/T2W = \quad (12)$$
$$\left\{ a_{1\,or\,2} \frac{1 - \exp(-TR/T_1)}{1 - \cos FA \cdot \exp(-TR/T_1)} \sin FA \right\} \Big/ \{a_{1\,or\,2} \exp(-TE/T_2)\} =$$
$$\frac{1 - \exp(-TR/T_1)}{1 - \cos FA \cdot \exp(-TR/T_1)} \sin FA / \exp(-TE/T_2) = f_3(T_1, T_2)$$

(Modification)

In the above description, an example has been described in which the image processing unit 230 of the MRI apparatus performs from parameter value estimation to myelin image generation. The function of the image processing unit 230 can be realized by an image processing apparatus 300 different from the MRI apparatus 100, and an MRI system may include the MRI apparatus 100 and the image processing apparatus 300.

Figure 8:
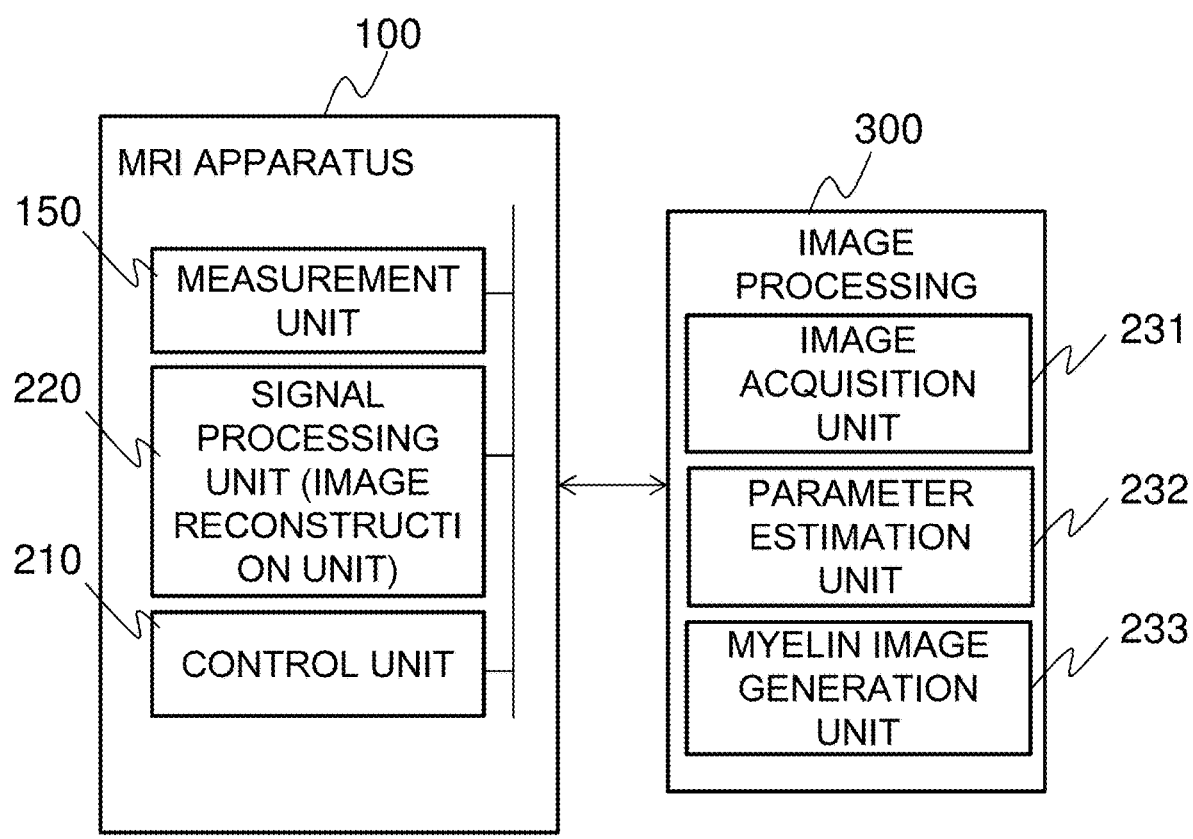
FIG. 8 is a block diagram illustrating a schematic configuration of an MRI system according to a modification of the invention.

For example, as illustrated in FIG. 8, the image processing apparatus 300 includes an image acquisition unit 231, a parameter estimation unit 232, and a myelin image generation unit 233. It is possible to adopt a configuration in which the image acquisition unit 231 acquires a reconstructed image from the MRI apparatus, the parameter estimation unit 232 estimates a T1 map and a T2 map based thereon, and the myelin image generation unit 233 generates a myelin image from the estimated T1 map and T2 map.

It is possible to adopt a configuration in which the image processing apparatus 300 acquires a T1 map and a T2 map generated in advance and generates a myelin image from the acquired T1 map and the T2 map using the myelin image generation unit 233 without estimating the T1 map and the T2 map.

In this MRI system, data exchange between the MRI apparatus 100 and the image processing apparatus 300 can employ well-known means such as wired or wireless data transmission/reception means or a portable medium. Further, the image processing apparatus 300 may be constructed in a cloud, etc., or may be constituted by a plurality of CPUs. As described above, by realizing a predetermined calculation function using a modality different from that of the MRI apparatus, a degree of freedom of the user can be increased and a load on the computer in the MRI apparatus can be reduced.

What is claimed is:

1. An MRI apparatus comprising:
   a measurement unit comprising:
      a magnet that generates a static magnetic field;
      a gradient magnetic field coil that generates a gradient magnetic field;
      a sequencer;
      a gradient magnetic field power supply;
      a high-frequency magnetic field generator;
      a transmission/reception coil that irradiates a high-frequency magnetic field and detects a nuclear magnetic resonance signal from a subject; and
      a receiver that detects the nuclear magnetic resonance signal from the subject;
   a display; and
   a computer coupled to the sequencer, the receiver, and the display, the computer programmed to:
   control the sequencer to control the measurement unit to measure the echo signal for each of a plurality of predetermined parameter sets and acquire k-space data for each predetermined parameter set, each parameter set includes imaging parameters including a repetition time (TR), an echo time (TE), a setting intensity (flip angle (FA)) of the high-frequency magnetic field, and a phase (θ) of the high-frequency magnetic field, and each of the plurality of predetermined parameter sets has different imaging parameters, reconstruct images by performing three-dimensional (3D) inverse Fourier transform on the collected k-space data, estimate a subject parameter value using a predetermined signal function and the reconstructed images by estimating a longitudinal relaxation time T1 or a longitudinal relaxation speed R1=1/T1 and a transverse relaxation time T2 or a transverse relaxation speed R2=1/T2 as quantitative values for each pixel, and generating T1 and T2 maps, generate a myelin image from the T1 map and the T2 map, and display the generated myelin image on the display.

2. The MRI apparatus according to claim 1, wherein the transverse relaxation speed includes an apparent transverse relaxation speed or includes a transverse relaxation speed calculated using the apparent transverse relaxation speed.

3. The image processing apparatus according to claim 1, wherein the function includes a product of the longitudinal relaxation speed and the transverse relaxation speed.

4. The MRI apparatus according to claim 1, wherein the computer is programmed to divide a pixel value of a T1-weighted image by a pixel value of a T2-weighted image, and the pixel value of the T1-weighted image and the pixel value of the T2-weighted image are calculated from the quantitative value.

5. The MRI apparatus according to claim 4,
wherein the T1-weighted image is obtained according to an expression for calculating a T1-weighted image from a T1 value, and
wherein the T2-weighted image is obtained according to an expression for calculating a T2-weighted image from a T2 value.

6. The MRI apparatus according to claim 1, wherein the signal function is generated by interpolating a result obtained by executing a numerical simulation for each of combinations of a plurality of different imaging parameters and subject parameters.

* * * * *